(12) United States Patent
Cloutier et al.

(10) Patent No.: US 9,030,211 B2
(45) Date of Patent: May 12, 2015

(54) CALIBRATION RESISTANCE EMULATOR

(75) Inventors: Jeffrey M. Cloutier, Thornton, CO (US); Julia M. Strandberg, Denver, CO (US); Tom Wilmering, Westminster, CO (US)

(73) Assignee: Covidien LP, Mansfield, MA (US)

( * ) Notice: Subject to any disclaimer, the term of this patent is extended or adjusted under 35 U.S.C. 154(b) by 759 days.

(21) Appl. No.: 13/307,727

(22) Filed: Nov. 30, 2011

(65) Prior Publication Data

US 2013/0134989 A1     May 30, 2013

(51) Int. Cl.
| | | |
|---|---|---|
| *G01R 35/00* | (2006.01) | |
| *A61B 5/1495* | (2006.01) | |
| *A61B 5/00* | (2006.01) | |
| *A61B 5/1455* | (2006.01) | |
| *A61B 5/053* | (2006.01) | |

(52) U.S. Cl.
CPC ......... *A61B 5/14551* (2013.01); *A61B 5/14552* (2013.01); *A61B 5/053* (2013.01); *A61B 5/1495* (2013.01)

(58) Field of Classification Search
CPC .. A61B 5/0408; A61B 5/053; A61B 5/14551; A61B 5/1495; A61B 2560/0223; A61B 2562/02
USPC ......... 324/601, 600, 202, 750.02, 750.01, 74, 324/130; 600/324, 323, 322, 312, 311, 310, 600/309
See application file for complete search history.

(56) References Cited

U.S. PATENT DOCUMENTS

| | | | | |
|---|---|---|---|---|
| 4,335,349 | A * | 6/1982 | Baldock et al. | 324/601 |
| 5,304,919 | A * | 4/1994 | Brown | 324/74 |
| 5,807,247 | A | 9/1998 | Merchant et al. | |
| 5,995,855 | A | 11/1999 | Kiani et al. | |
| 6,351,658 | B1 | 2/2002 | Middleman et al. | |
| 6,490,466 | B1 | 12/2002 | Fein et al. | |
| 6,571,113 | B1 | 5/2003 | Fein et al. | |
| 6,584,336 | B1 | 6/2003 | Ali et al. | |
| 6,597,933 | B2 | 7/2003 | Kiani et al. | |
| 7,106,067 | B2 * | 9/2006 | Quackenbush et al. | 324/446 |
| 7,500,950 | B2 | 3/2009 | Al-Ali et al. | |
| 7,809,419 | B2 | 10/2010 | Fein et al. | |
| 2009/0247852 | A1 | 10/2009 | Boyce et al. | |

* cited by examiner

*Primary Examiner* — Hoai-An D Nguyen
(74) *Attorney, Agent, or Firm* — Fletcher Yoder PC

(57) ABSTRACT

The present disclosure relates generally to patient monitoring systems and, more particularly, to a resistance emulator for patient monitors. In an embodiment, a resistance emulator includes a first plug configured to couple with a medical monitor. The medical monitor is configured to receive a calibration resistance value of a medical device sensor from a coded resistor. The resistance emulator further includes a second plug configured to couple with a medical device sensor. The medical device sensor is configured without the coded resistor. The resistance emulator also includes emulation circuitry configured to provide an emulated signal representative of the calibration resistance value to the medical monitor.

20 Claims, 4 Drawing Sheets

CALIBRATION RESISTANCE EMULATOR

BACKGROUND

The present disclosure relates generally to medical monitor adapters and, more particularly, to adapters for medical monitors that emulate a sensor calibration signal from a coded resistor value.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. To allow such monitoring, various types of sensors and monitors may be employed by caregivers. For example, to measure certain characteristics, optical based sensors may be utilized that transmit electromagnetic radiation, such as light, through a patient's tissue and then photoelectrically detect the absorption and scattering of the transmitted or reflected light in such tissue. The physiological characteristics of interest may then be calculated based upon the amount of light absorbed and/or scattered or based upon changes in the amount of light absorbed and/or scattered. In such measurement approaches, the light passed through the tissue is typically selected to be of one or more wavelengths that may be absorbed and/or scattered by one or more constituents of the blood or tissue in an amount correlative to the amount of the constituents present in the blood or tissue.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin ($SpO_2$) in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. As noted above, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

The light sources used in pulse oximeters, as well as other medical devices, may be designed to emit wavelengths that correspond to the physiological characteristics to be determined. For example, pulse oximeters may utilize light sources that emit in at least two spectral regions, one that emits in the red region (typically about 660 nm) and one in the near infrared region (typically about 900 nm). The absorbance ratios for these wavelengths can then be used to determine the oxygenation of a patient's blood. In another example, some pulse oximeters may replace the 660 nm emitter with an emitter designed to emit light in the far red region (typically about 730 nm). The 730 nm emitter may then be used in conjunction a 900 nm emitter to determine the oxygenation of a patient's blood. The use of a 730 nm emitter and a 900 nm emitter may provide greater accuracy when $SpO_2$ is low (e.g., in the range below 75%).

The wavelengths emitted by the sensors can vary between sensors. For example, due to manufacturing variations, light sources, such as light emitting diodes (LEDs) or laser diodes, may emit slightly different wavelengths, may vary in chromaticity, and may have varied color temperatures. Accordingly, calibration models may be included in pulse oximeters to account for these variations. To account for these differences, the LEDs may be bin sorted based upon their variances and then selected for incorporation into the sensor. The bin sorting process may be extremely time consuming and costly because the process may require evaluation of individual LEDs for specific parameters. Previously, various calibration coefficients were programmed into the monitor and a proper coded resistor was selected and placed in the sensor to convey the correct code to the medical device monitor so that it could select the proper calibration coefficients based upon the specific properties of the LEDs.

More recently, however, many pulse oximeter monitors determine the proper calibration for sensors by reading calibration coefficients from the digital memory in the sensors, and thus do not read a coded resistor. However, many legacy monitors still determine the proper calibration by reading coded resistor values provided by the coded resistor in the sensors, thus many sensors continue to include coded resistors in addition to digital memories so that the sensors may be used with legacy monitors as well as the more recent monitors. The inclusion of such coded resistors in the sensors can complicate manufacturing and introduce additional costs.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to systems that enable calibration of legacy medical monitors that determine sensor calibration coefficients through coded resistors in a sensor when such a resistor is not included in the sensor. Legacy medical monitors have utilized coded resistors in medial sensors to determine proper calibration coefficients. These monitors typically provide a voltage across a coded resistor in a sensor and read the resultant current to determine the resistor value. These monitors then correlate the resistor value with corresponding calibration coefficients in a lookup table stored in the monitor and the selected coefficients are used in the monitor's algorithms.

The present disclosure enables the legacy medical monitors to be calibrated despite a lack of the coded resistor in the sensor. The resistor-free calibration may be enabled through a resistance emulator designed to emulate a calibration resistor value of the sensor when no coded resistors are included in the sensor. Calibration data is provided to a resistance emulator (e.g., a microprocessor) from a digital memory of the sensor. In certain embodiments, the calibration data includes calibration coefficients and/or calibration curves that correlate to specific resistor values. In other embodiments, the calibration data may include stored representations of specific resistor values for the sensor. The resistance emulator determines a proper resistor value based upon the calibration data and provides a signal correlative to the resistor value to the legacy medical monitor.

Figure 1:
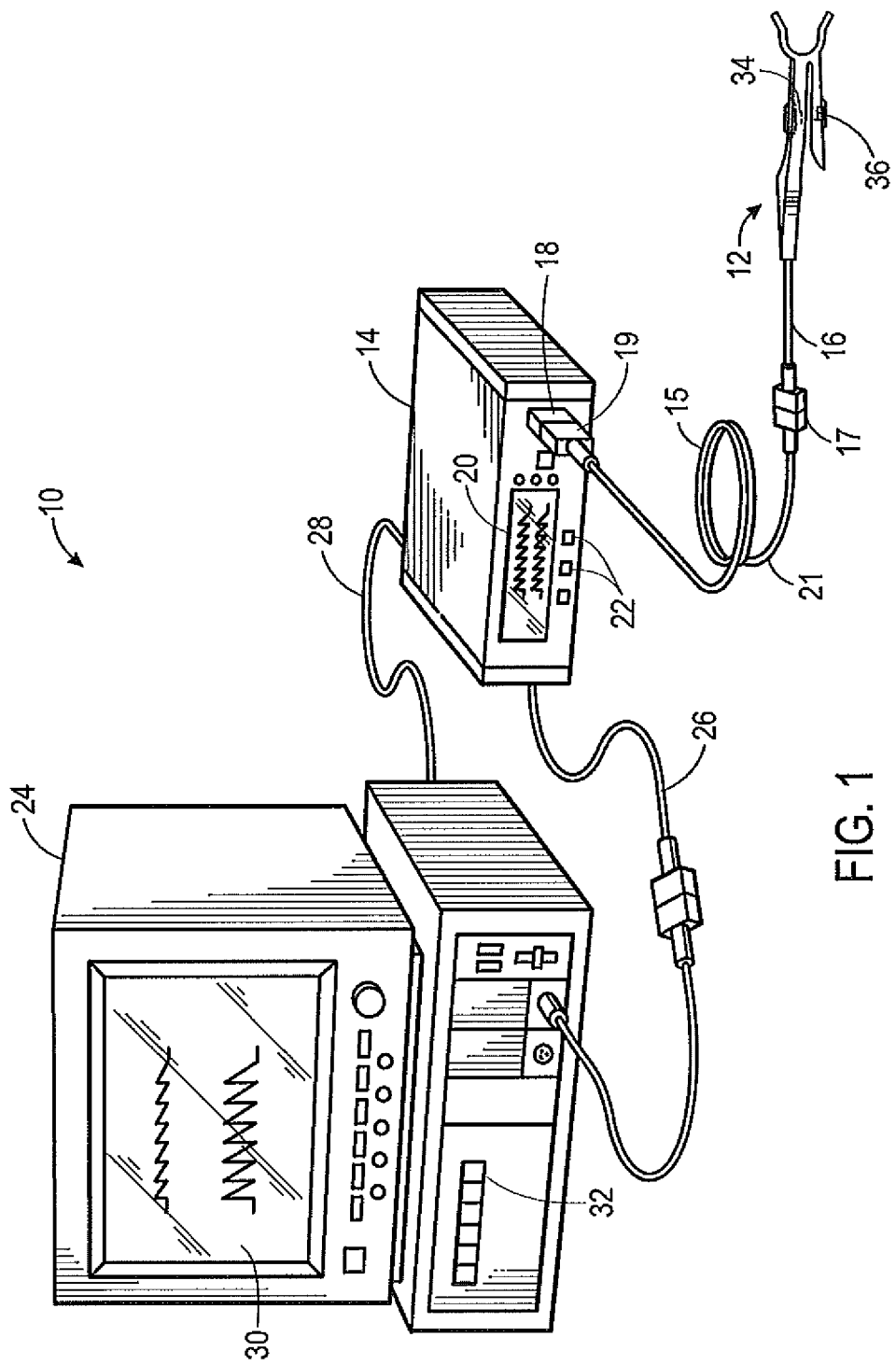
FIG. 1 is a perspective view of a medical monitoring system that includes a resistance emulator, a sensor that does not include a coded resistor, and a monitor that determines sensor calibration curves by reading a coded resistor value.
Figure 1A:
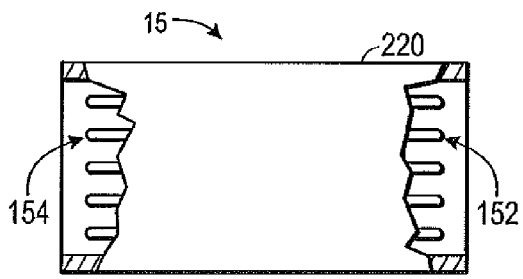
FIG. 1a is a partially broken side view of a resistance emulator that does not include a cable.

With the foregoing considerations in mind, FIG. 1 depicts a medical monitoring system, such as a pulse oximetry system 10, having a sensor 12 coupled to a monitor 14, such as a legacy monitor, in accordance with an embodiment of the present disclosure. The sensor 12 may be coupled to the monitor 14 via a resistance emulator 15, as will be discussed further below with respect to FIG. 2. The resistance emulator 15 may couple a sensor cable 16 with a sensor connector 18. As depicted, the resistance emulator 15 may include connectors 17 and 19 interconnected by a cable 21 such that the distance between the sensor cable 16 and the sensor connector 18 may be extended. In this embodiment, the resistance emulation circuitry discussed below may reside in the connector 17, the connector 19, the cable 21 or any combination thereof. However, in other embodiments, it may be desirable for the resistance emulator 15 to occupy less space. In such embodiments, as depicted in FIG. 1A, the resistance emulator 15 may not include the cable, but instead include an enclosure 220 that contains the resistance emulation circuitry discussed in detail below. The monitor 14 may be any legacy monitor, such as those previously available from Nellcor Puritan Bennett L.L.C., of Boulder, Colo. or other manufacturers, such as Koninklijke Philips Electronics N.V. The monitor 14 may be configured to calculate physiological parameters from signals received from the sensor 12 when the sensor 12 is placed on a patient. For example, the monitor 14 may be configured to determine physiological characteristics, such as the blood-oxygen saturation of hemoglobin in arterial blood, the volume of individual blood pulsations supplying the tissue, and/or the rate of blood pulsations corresponding to each heartbeat of a patient. Further, in certain embodiments, the monitor 14 may be configured to determine other physiological parameters, such as respiratory rate, respiratory effort, continuous non-invasive blood pressure, cardiovascular effort, glucose levels, level of consciousness, total hematocrit, hydration, electrocardiography, temperature, or any other suitable physiological parameter.

The monitor 14 may include a display 20 configured to display information regarding the physiological parameters, information about the system, and/or alarm indications. For example, the display 20 may be configured to display computed physiological data such as an oxygen saturation percentage, a pulse rate, and/or a plethysmographic waveform. The monitor 14 also may include various input components 22, such as knobs, switches, keys and keypads, buttons, etc., to provide for operation and configuration of the monitor.

In certain embodiments, the monitor 14 may be coupled to a multi-parameter patient monitor 24 to provide additional functionality. For example, the monitor 14 may be connected to the multi-parameter patient monitor 24 via a cable 26 connected to a sensor input port or via a cable 28 connected to a digital communication port. In addition to the monitor 14, or alternatively, the multi-parameter patient monitor 24 may be configured to calculate physiological parameters and to provide a central display 30 for information from the monitor 14 and from other medical monitoring devices or systems. In some embodiments, the monitor 24 may be configured to display and/or determine some or all of the same physiological parameters as monitor 14. The monitor 24 also may include various input components 32, such as knobs, switches, keys and keypads, buttons, etc., to provide for operation and configuration of the monitor 24. Further, the monitor 14 and/or the multi-parameter patient monitor 24 may be connected to a network to enable the sharing of information with servers or other workstations.

The sensor 12 may be any sensor suitable for detection of any physiological parameter. According to certain embodiments, the sensor 12 may be configured for photoelectric detection of blood and tissue constituents. For example, the sensor 12 may be a pulse oximetry sensor, such as those available from Nellcor Puritan Bennett, L.L.C. The sensor 12 may include an emitter 34 for emitting light at certain wavelengths into a patient's tissue and a detector 36 for detecting the light after it is reflected and/or absorbed by the patient's tissue. Further, the sensor 12 may include additional components, such as acoustic transducers or microphones, electrodes for measuring electrical activity or potentials (such as for electrocardiography), pressure sensors, motion sensors, and temperature sensors, among others.

As shown in FIG. 1, the sensor 12 may be a clip-type sensor suitable for placement on an appendage of a patient, e.g., a digit, an ear, etc. In other embodiments, the sensor 12 may be a bandage-type sensor having a generally flexible sensor body to enable conformable application of the sensor to a sensor site on a patient. In yet other embodiments, the sensor 12 may be secured to a patient via adhesive (e.g., in an embodiment having an electrode sensor) on the underside of the sensor body or by an external device, such as headband or other elastic tension device. In yet other embodiments, the sensor 12 may be a configurable sensor capable of being configured or modified for placement at different sites (e.g., multiple tissue sites, such as a digit, a forehead of a patient, etc.). Further, in certain embodiments, the system 10 may include multiple sensors instead of the single sensor 12.

If it is a legacy monitor, the monitor 14 may expect to receive a resistance value from the sensor 12 to calibrate the sensor 12 with the monitor 14. However, the sensor 12 does not include a coded resistor that provides the resistance value, but instead may include an encoder 42 that may include a memory, such as an erasable programmable read only memory (EPROM), that provides calibration data. As will be discussed in more detail below, the resistance emulator 15 may include a microprocessor useful for correlating the calibration data sent from the encoder 42 of the sensor 12 with a proper resistance value to send to the monitor 14. The resistance emulator 15 may then emulate the resistance value by providing an electrical current that is interpretable by the monitor 14. For example, the resistance emulator 15 may receive calibration coefficients and/or calibration curves from the encoder 42. The resistance emulator 15 may include a lookup table that correlates calibration coefficients and/or calibration curves with corresponding resistance values. Based upon the calibration coefficients and/or the calibration curve provided from the encoder 42 and the lookup table, the resistance emulator 15 may derive and emulate the proper resistance value that corresponds with the light emitting elements on that particular sensor 12. The emulated resistance value is sent to the monitor 14 in the form of an electrical current. Thus, the monitor 14 may be calibrated to operate optimally with the sensor 12, despite the lack of a coded resistor in the sensor 12.

Figure 2:
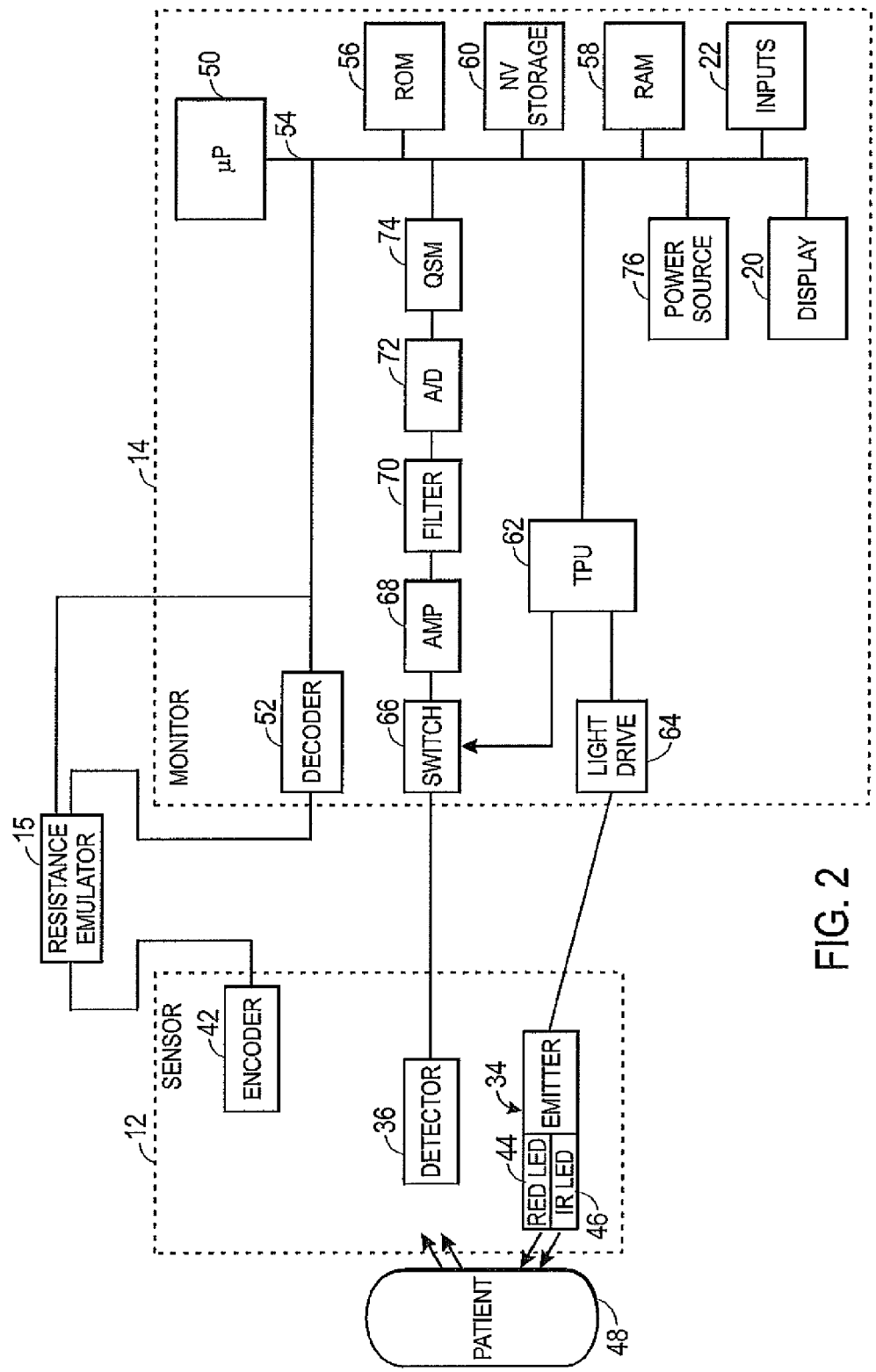
FIG. 2 is a block diagram of the medical monitor, the resistance emulator, and the sensor of FIG. 1, in accordance with certain embodiments.

Benefits of the resistance emulator 15 may be more clearly shown though illustrating certain components of the medical monitoring system 10. Turning to FIG. 2, a simplified block diagram of a portion of the medical monitoring system 10 is illustrated, in accordance with certain embodiments. Specifically, certain components of the sensor 12, the monitor 14, and the resistance emulator 15 are illustrated in FIG. 2. The sensor 12 includes the emitter 34, the detector 36, and an encoder 42. The emitter 34 includes two light sources 44 and 46, shown here as LEDs, that are capable of emitting different wavelengths of light into the tissue of a patient 48 to measure physiological parameters of the patient 48. As shown in FIG. 2, the light source 44 represents a red LED designed to emit red light at a wavelength between about 600 nanometers (nm) and about 700 nm, and the light source 46 represents an infrared (IR) LED designed to emit IR light at a wavelength between about 800 nm and about 1000 nm. However, in other embodiments, the light sources 44 and 46 may be designed to emit light at other suitable wavelengths.

It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. In operation, light enters the detector 36 after passing through the tissue of the patient 48. The detector 36 may convert the light at a given intensity, which may be directly related to the absorbance and/or reflectance of light in the tissue of the patient 48, into an electrical signal. That is, when more light at a certain wavelength is absorbed or reflected, less light of that wavelength is typically received from the tissue by the detector 36. For example, the detector 36 may include one or more photodiodes, or any other element capable of converting light into either a current or voltage. After converting the received light to an electrical signal, the detector 36 may send the signal to the monitor 14, where physiological characteristics may be calculated based at least in part on the absorption of light in the tissue of the patient 48.

Signals from the detector 36 may be transmitted to the monitor 14 where the signals can be used to calculate the patient's physiological characteristics. The monitor 14 generally includes the one or more processors 50 connected to an internal bus 54. The bus 54 is also connected to the input components 22 and the display 20, as well as a read-only memory (ROM) 56, a random access memory (RAM) 58, and a nonvolatile storage 60 (such as a magnetic or solid state hard drive or memory, optical disk, or any other suitable optical, magnetic, or solid-state computer readable media) that stores longer-term data.

A time processing unit (TPU) 62 may provide timing control signals to a light drive circuitry 64, which controls when the emitter 34 is illuminated and the multiplexed timing for the light sources 44 and 46. The TPU 62 also may control the gating-in of signals from detector 36 through a switching circuit 66. These signals may be sampled at the proper time, depending upon which light source 44 or 46 is illuminated. The received signal from the detector 36 may be passed through an amplifier 68, a low pass filter 70, and an analog-to-digital converter 72 for amplifying, filtering, and digitizing the electrical signals the from the sensor 12. The digital data may then be stored in a queued serial module (QSM) 74 for later downloading to the RAM 58 as the QSM 74 fills up. In certain embodiments, there may be multiple separate parallel paths having the amplifier 68, the filter 70, and the A/D converter 72 for multiple light wavelengths or spectra received.

The processor 50 may use the digital data, as well as other signals from the detector 36 to calculate and/or determine physiological characteristics, such as oxygen saturation, pulse rate, and total hemoglobin, among others. For example, the processor 50 may use various encoded instructions, algorithms, and/or lookup tables that may be stored in the ROM 56, as well as in the nonvolatile storage 60, to calculate the physiological characteristics based at least in part upon the signals that correspond to the light received by the detector 36. According to certain embodiments, code encoding executable algorithms may be stored in the ROM 56 or the nonvolatile storage 60 and accessed and operated according to processor instructions. The calculated physiological characteristic may then be displayed on the display 20 for a caregiver to monitor or review.

The sensor 12 also includes the encoder 42, which contains information about the sensor 12, such as the sensor type (e.g., whether the sensor is intended for placement on a forehead, digit, or other body part) and the wavelengths of light emitted by the light sources 44 and 46. The sensor information may allow the monitor 14 to select appropriate algorithms and/or calibration coefficients for calculating the physiological characteristics of the patient 48. According to certain embodiments, the encoder 42 may include memory on which one or more of the following information may be stored for communication to the monitor 14: the type of the sensor 12; the wavelengths of light emitted by the light sources 44 and 46; and calibration data, such as the proper calibration coefficients, calibration curves, and/or algorithms to be used for calculating the physiological characteristics of the patient 48. The calibration data may also include data representative of a coded resistor value that may be emulated by the resistance emulator 15.

The calibration data from the encoder 42 can be transmitted to the resistance emulator 15, where the data can be used to determine a current to be sent to a decoder 52 of the monitor 14. For example, as discussed further below with respect to FIG. 4, a microprocessor 156 of the resistance emulator 15 may use the digital calibration data from the encoder 42 to determine a proper resistance value to emulate for a monitor 14. The resistance emulator 15 may then emulate the resistance value by providing an electrical current corresponding to the resistance value to the monitor 14.

Upon reaching the monitor 14, the emulated resistance value (e.g., the electrical current) is then provided to a decoder 52 expecting the electrical current corresponding to a coded resistance value. The decoder 52 may decode the emulated resistance value and may provide the decoded information to the processor 50. The processor 50 may then use the decoded information to determine the proper method for calculating the patient's physiological characteristics. For example, the processor may use the decoded information in conjunction with algorithms or look-up tables to identify the proper calibration coefficients and/or algorithms to be used for calculating the patient's physiological characteristics.

The monitor 14 further includes a power source 76 that may be used to transmit power to the components located in the monitor 14 and/or the sensor 12. In one embodiment, the power source 76 may be one or more batteries, such as a rechargeable battery. The battery may be user-removable or may be secured within the housing of the monitor 14. Use of a battery may, for example, allow the monitor 14 to be highly portable, thus allowing a user to early and use the monitor 14 in a variety of situations and locations. Additionally, the power source 76 may include AC power, such as provided by an electrical outlet, and the power source 76 may be connected to the AC power via a power adapter through a power cord (not shown). This power adapter may also be used to directly recharge one or more batteries of the power source 76 and/or to power the monitor 14.

Figure 4:
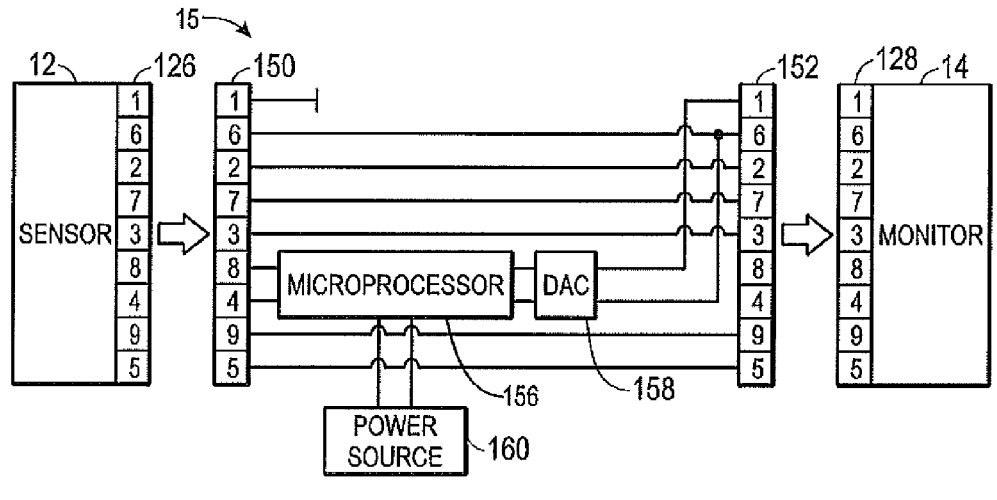
FIG. 4 is a schematic view of the resistance emulator of FIG. 1, in accordance with certain embodiments.

To provide the various tasks detailed below, the microprocessor 156 may use a power source 160 (as illustrated in FIG. 4). In certain embodiments, power to the power source 160 may be provided by the power source 76 of the medical monitor 14. According to certain embodiments, the power source 76 may include DC power that can be provided to the microprocessor 156 of the resistance emulator 15. For example, the power source 76 may include an AC/DC converter that converts AC power provided by an electrical outlet to DC power. According to certain embodiments, the processor 50 may control the level of power provided to the microprocessor 156 from the power source 76. For example, the processor 50 may employ one or more algorithms and/or instructions stored in the ROM 56 or the nonvolatile storage 60 to determine the level of power that should be provided to the microprocessor 156 of the resistance emulator 15. Further, in certain embodiments, the processor 50 may employ linear control or pulse width modulation (PWM) control to govern the level of power provided to the microprocessor 156 of the resistance emulator 15. In certain embodiments the power source 160 may include a capacitor that is charged during system 10 startup, may obtain power from a battery, or may use ambient light from a solar cell. Once the monitor 14 receives the emulated resistance value, the resistance emulator 15 may not be needed for further calibration of the monitor 14. Thus, in certain embodiments, power may be conserved by only supplying power to the resistance emulator 15 during the determination, generation, and provision of the emulated resistance value to the monitor 14.

Figure 3:
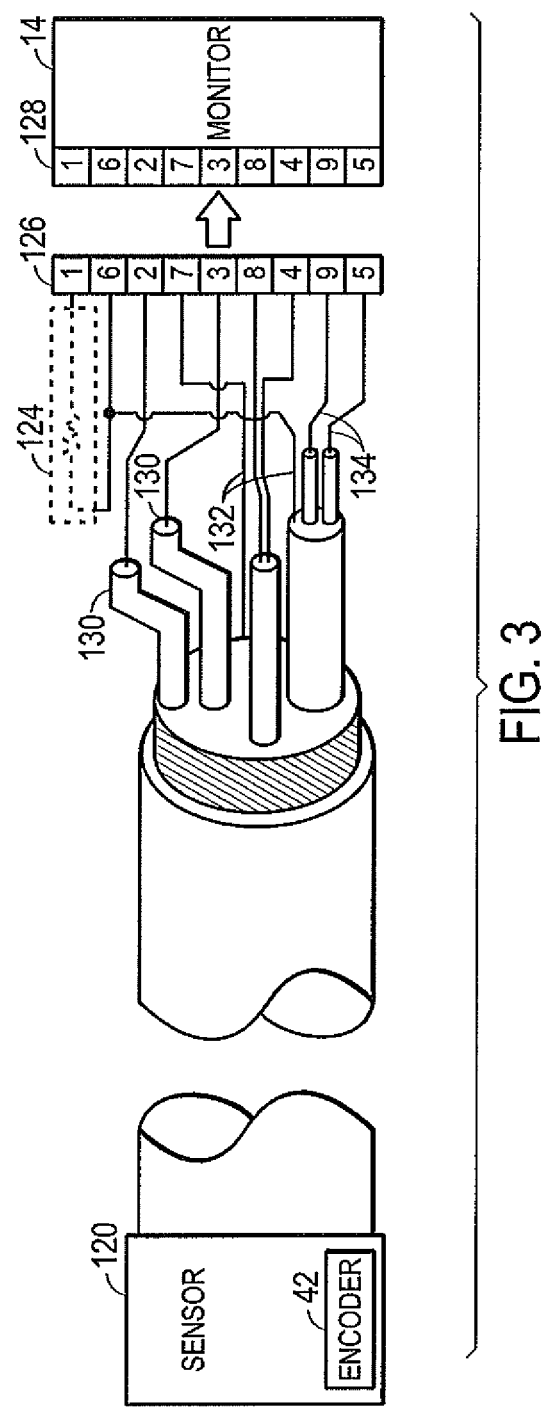
FIG. 3 is a schematic view of a sensor without a coded resistor for providing the calibration data of the sensor, in accordance with an embodiment.

FIG. 3 illustrates a sensor 12 configured with the encoder 42 but without a coded resistor 124. In the provided example, the dashed line illustrates where the coded resistor 124 would be expected by the monitor 14 that receives calibration data from the coded resistor 124. As illustrated in the embodiment of FIG. 3, the sensor 12 includes a pin configuration 126 that is compatible with a pin configuration 128 of the monitor 14. The sensor 12 may include emitter lines 130, a shield 132, and detector lines 134. For example, in the depicted example, the sensor 12 includes emitter lines 130 that pass through pins 2 and 3 of the pin configuration 128. The emitter lines 130 may provide emitter 34 control from the light drive 64 of the monitor 14. Further, the sensor 12 includes encoder lines 133 that pass through pins 4 and 8. The sensor 12 may also include detector lines 134 that pass through pins 5 and 9. The sensor 12 also includes a shield 132 that encompasses the detector lines 134 to prevent electromagnetic interference crosstalk from the emitter lines 130.

As previously discussed, the monitor 14 may be a legacy monitor that expects to receive calibration data in the form of a resistance value generated from a coded resistor 124 of the sensor 12. However, when the coded resistor 124 is not present in the sensor 12, as illustrated, the monitor 14 may be provided with the calibration data through the resistance emulator 15. For example, FIG. 4 illustrates an embodiment of the resistance emulator 15 configured to provide an emulated resistance value to the monitor 14 when a coded resistor 124 is not present in the sensor 12. The resistance emulator 15 includes a sensor pin configuration 150 that is compatible with the pin configuration 126 of sensor 12. Further, the resistance emulator 15 includes a monitor pin configuration 152 that is compatible with the pin configuration 128 of the sensor connector 18 of the monitor 14.

In the provided example, the monitor 14 expects to receive a coded resistance value from pin 1 of the pin configuration 128. Further, the monitor 14 expects to receive signals from the emitter lines 130 at pins 2 and 3 and signals from the detector lines 134 at pins 5 and 9. The emitter lines 130, shield 132, and detector lines 134 are each passed from the sensor pin configuration 150 to the monitor pin configuration 152 (e.g., the emitter lines 130 are passed through to pins 2 and 3 and the detector lines 134 are passed through to pins 5 and 9). However, because the sensor 12 does not include a coded resistor 124, pin 1 of the sensor pin configuration 150 is not passed through to the monitor pin configuration 152. Instead, the microprocessor 156 of the resistance emulator 15 is enabled to generate a digital signal based upon the resistance value for the sensor 12. For example, the microprocessor 156 may be coupled to a digital-to-analog converter 158, and the digital-to-analog converter 158 may convert the digital signal from the microprocessor 156 into an analog signal. In certain embodiments, the digital-to-analog converter 158 may provide a current that is interpretable by the medical monitor 14 as being correlative to an appropriate coded resistor value. As will be discussed in more detail below, the resistance emulator 15 provides the current signal to the pin or pins where the monitor 14 expects to receive the coded resistance value (e.g., pin 1).

Figure 5:
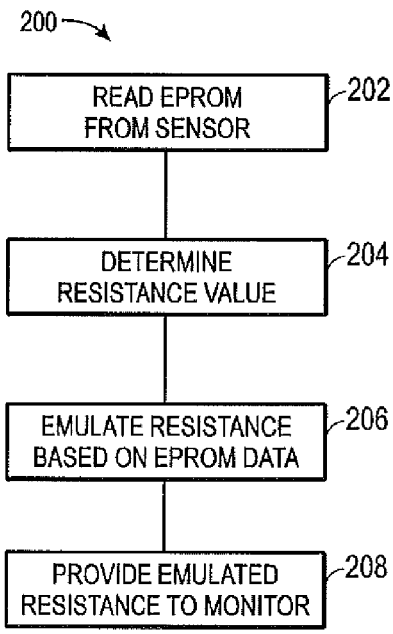
FIG. 5 is a flowchart illustrating a process of emulating a calibration resistor of a medical sensor, in accordance with an embodiment.

FIG. 5 depicts a process 200 that may be employed to enable calibration of a legacy medical monitor 14 configured to receive calibration data from the coded resistor 124 when the calibration data is stored in memory of the sensor 12. The method 200 may begin by reading (block 202) calibration data from the encoder 42 in the sensor 12. For example, in the depicted embodiment of FIG. 4, the microprocessor 156 receives calibration data from memory of the encoder 42 of the sensor 12 over pins 4 and 8. The calibration data stored on the memory of the encoder 42 may include calibration coefficients, a calibration curve, and/or or a coded resistor value for the sensor 12, for example.

The resistance emulator 15 may then determine (block 204) an appropriate resistance value that correlates with the calibration data. When the resistance emulator 15 is provided with calibration coefficients and/or a calibration curve, the microprocessor 156 of the resistance emulator 15 may determine the proper resistance value by correlating the calibration coefficients and/or the calibration curve to a specific resistance value (e.g., through a lookup table). In certain embodiments, the resistance emulator 15 may be provided the proper resistance value from the encode 42, thus requiring no conversion of the calibration data to a proper resistance value by the microprocessor 156.

The resistance emulator 15 emulates (block 206) a resistance signal based upon the determined appropriate resistance value. To emulate the resistance value, an electrical current correlating to appropriate resistance value may be generated by the resistance emulator 15. For example, as previously discussed, the microprocessor 156 may provide a digital signal representative of the appropriate resistance value to a digital-to-analog converter 158. In certain embodiments, the digital-to-analog converter 158 generates an electrical current based upon the digital signal. In other embodiments, the digital-to-analog converter 158 may generate a voltage based upon the digital signal. The voltage may be provided to a voltage-to-current converter 159 that generates an electrical current based upon the voltage.

The electrical current is provided to monitor 14 at the pin or pins where the resistance value is expected by the monitor 14 (block 208). As previously discussed, in the illustrated example of FIG. 3, the monitor 14 may expect the electrical current at pin 1. Thus, the resistance emulator 15 provides an output line to pin 1 of the monitor pin configuration 152 to provide the generated electrical current to the monitor 14. By providing the generated electrical current to the monitor 14, the monitor 14 is enabled to receive calibration data in the expected format. Thus the monitor 14 is enabled to determine calibration coefficients despite the lack of a coded resistor 124 in the sensor 12.

While the disclosure may be susceptible to various modifications and alternative forms, specific embodiments have been shown by way of example in the drawings and will be described in detail herein. However, it should be understood that the disclosure is not intended to be limited to the particular forms disclosed. Rather, the disclosure is to cover all modifications, equivalents and alternatives falling within the spirit and scope of the disclosure as defined by the following appended claims.

What is claimed is:

1. A resistance emulator comprising:
a first plug configured to couple with a medical monitor configured to receive a calibration resistance value from a coded resistor of a medical sensor, wherein the first plug comprises a first plurality of pins in a pin configuration;
a second plug configured to couple with a medical sensor configured without the coded resistor, wherein the second plug comprises a second plurality of pins in the pin configuration; and
emulation circuitry configured to receive calibration data from a memory of the medical sensor through a first pin and a second pin of the first plurality of pins and to provide a signal correlative to the calibration resistance value to the medical monitor through a third pin of the second plurality of pins, wherein the first, second, and third pins each comprise a different pin position in the pin configuration.

2. The resistance emulator of claim 1, wherein the emulation circuitry comprises:
a microprocessor configured to:
read the calibration data from the memory of the medical sensor, and
generate the signal correlative to the calibration resistance value based at least in part upon the calibration data, the signal being a digital signal.

3. The resistance emulator of claim 2, wherein the emulation circuitry comprises a digital-to-analog converter configured to convert the digital signal into an analog signal.

4. The resistance emulator of claim 1, wherein the first plug, the second plug, and the emulation circuitry are disposed in a housing.

5. The resistance emulator of claim 3, wherein the analog signal comprises a current interpretable by the medical monitor.

6. The resistance emulator of claim 2, wherein the calibration data comprises calibration coefficients, calibration curves, or a calibration algorithm, or any combination thereof, and the microprocessor is configured to determine the calibration resistance value from the calibration data.

7. The resistance emulator of claim 5, wherein the emulation circuitry comprises a lookup table configured to correlate the calibration data to corresponding calibration resistance values, and wherein the microprocessor is configured to query the lookup table to determine the calibration resistance value corresponding to the calibration data.

8. The resistance emulator of claim 1, comprising a cable disposed between the first and second plugs, the cable configured to transfer signals between the first and second plugs.

9. The resistance emulator of claim 1, comprising a power source comprising a solar cell.

10. A method of manufacturing a resistance emulator, comprising:
providing a first plug configured to couple with a medical monitor configured to receive a calibration resistance value from a coded resistor of a medical sensor, wherein the first plug comprises a first plurality of pins in a pin configuration;
providing a second plug configured to couple with a medical sensor configured without the coded resistor, and wherein the second plug comprises a second plurality of pins in the pin configuration; and
providing emulation circuitry configured to receive calibration data from a memory of the medical sensor through a first pin and a second pin of the first plurality of pins and to provide a signal correlative to the calibration resistance value to the medical monitor through a third pin of the second plurality of pins, wherein the first, second, and third pins each comprise a different pin position in the pin configuration.

11. The method of claim 10, comprising providing a cable between the first and second plugs, wherein the cable is configured to transfer signals between the first and second plugs.

12. The method of claim 10, comprising providing a microprocessor configured to:
read the calibration data from the memory of the medical sensor, and
generate the signal correlative to the calibration resistance value based at least in part upon the calibration data, the signal being a digital signal.

13. The method of claim 12, comprising:
providing a digital-to-analog converter configured to convert the digital signal to a current interpretable by the medical monitor.

14. A method, comprising:
reading, via a resistance emulator, calibration data from a memory of a medical sensor;
generating, via the resistance emulator, a signal correlative to a calibration resistance value, wherein the signal is interpretable by a medical monitor configured to receive the calibration resistance value from a coded resistor of the medical sensor;

providing, via the resistance emulator, the signal to the medical monitor; and providing, via a power source of the resistance emulator, power to the resistance emulator, wherein a level of the power provided to the resistance emulator is controlled via a processor of the medical monitor.

15. The method of claim 14, comprising:

receiving the calibration data at a microprocessor of the resistance emulator; and generating, via the microprocessor, a digital signal correlative to the calibration resistance value.

16. The method of claim 15, comprising stopping, via the power source of the resistance emulator, supply of the power to the resistance emulator after the resistance emulator provides the signal to the medical monitor.

17. The method of claim 15, wherein reading the calibration data from the memory of the medical sensor comprises receiving the calibration data through a first pin and a second pin of a first plug of the resistance emulator, wherein the first plug comprises a first plurality of pins in a pin configuration, and wherein providing the signal to the medical monitor comprises providing the signal through a third pin of a second plug of the resistance emulator, wherein the second plug comprises a second plurality of pins in the pin configuration, and wherein the first, second, and third pins each have a different pin position in the pin configuration.

18. The method of claim 14, wherein the calibration resistance value comprises an electrical current.

19. The method of claim 18, comprising converting the digital signal provided by the microprocessor into the electrical current via a digital-to-analog converter.

20. The method of claim 15, wherein generating the digital signal comprises comparing the calibration data to calibration resistance values in a look up table.

* * * * *